(12) United States Patent
Keränen et al.

(10) Patent No.: US 6,344,341 B1
(45) Date of Patent: Feb. 5, 2002

(54) INCREASED PRODUCTION OF SECRETED PROTEINS BY RECOMBINANT YEAST CELLS

(75) Inventors: Sirkka Keränen; Jaana Toikkanen, both of Helsinki; Ville Tieaho, Järvenpää; Hans Söderlund, Espoo, all of (FI)

(73) Assignee: Valtion teknillinen tetkimuskeskus, Espoo (FI)

( * ) Notice: Subject to any disclaimer, the term of this patent is extended or adjusted under 35 U.S.C. 154(b) by 0 days.

(21) Appl. No.: 09/446,920
(22) PCT Filed: Jul. 8, 1998
(86) PCT No.: PCT/FI98/00576
   § 371 Date: Dec. 30, 1999
   § 102(e) Date: Dec. 30, 1999
(87) PCT Pub. No.: WO99/02716
   PCT Pub. Date: Jan. 21, 1999

(30) Foreign Application Priority Data

Jul. 9, 1997 (FI) .................................. 972909

(51) Int. Cl.[7] .............................. C12P 21/06; C12N 1/16
(52) U.S. Cl. .................................. 435/69.1; 435/254.21
(58) Field of Search ............................. 435/69.1, 254.2

(56) References Cited

FOREIGN PATENT DOCUMENTS

EP 0284044 9/1988

OTHER PUBLICATIONS

Beckmann, Roland et al, AN 1998:1995 CAPLUS.
Broughton, Jon et al, AN 1997:751535 CAPLUS.
Piemper, Richard et al, AN 1997:572386 CAPLUS.
Wilkinson, Barrie M. et al, AN 1997:544618 CAPLUS.
Pilon, Marinus et al, AN 1997:544617 CAPLUS.
Dierks, Thomas et al, AN 1997:85383 CAPLUS.
Daimon, Makoto et al, AN 1997:26972 CAPLUS.
Hanein, Dorit et al, AN 1996:702981 CAPLUS.
Wilkinson, Barrie M. et al, AN 1996:623638 CAPLUS.
Iwasaki, Kouichi et al, AN 1996:484195 CAPLUS.
Biederer, Thomas et al, AN 1996:318034 CAPLUS.
Boisrame, Anita et al, AN 1996:309665 CAPLUS.
Koning, Ann J. et al, AN 1996:294167 CAPLUS.
Toikkanen, Jaana et al, AN 1996:286760 CAPLUS.
Finke, Kerstin et al, AN 1996:247557 CAPLUS.
Ng, Davis T. W. et al, AN 1996:119730 CAPLUS.
Panzner, Steffen et al, AN 1995:585384 CAPLUS.
Stirling, Colin J. et al, AN 1993:187399 CAPLUS.
Jaana Toikkanen et al, Yeast, vol. 12, 1996, pp. 425–438.
Kerstin Finke et al, The EMBO Journal, vol. 15, No. 7, 1996, pp. 1482–1494.
Steffen Panzner et al, Cell, vol. 81, May 1995, pp. 561–570.
Hanein, Dorit et al., Cell, vol. 87, 1996, pp. 721–732.

(List continued on next page.)

*Primary Examiner*—Robert A. Schwartzman
*Assistant Examiner*—Katharine F Davis
(74) *Attorney, Agent, or Firm*—Birch, Stewart, Kolasch & Birch, Ltd.

(57) ABSTRACT

This invention relates to recombinant-DNA-technology. Specifically this invention relates to new recombinant yeast cells transformed with SEB1 gene. Yeast cells transformed with several copies of SEB1 gene, or overexpressing the Seb1 protein by some other means, have an increased capacity to produce secreted foreign or endogenous proteins. Further, said new recombinant cells, when transformed with genes expressing suitable hydrolytic enzymes can utilize appropriate macromolecular compounds more efficiently, which results in increased cell mass production and/or more versatile utilization of the compounds in relevant biotechnical applications.

6 Claims, 8 Drawing Sheets2

OTHER PUBLICATIONS

Buckholz, Richard G. et al., Bio/Technology, vol. 9, 1991, pp. 1067–1072.
Martegani, E. et al., Appl. Microbiol. Biotechnol., vol. 37, 1992, pp. 604–608.
Sakai, Akira et al., Genetics, vol. 119, 1988, pp. 499–506.
Shuster, Jeffrey R., Gene., vol. 83, 1989, pp. 47–55.
Sleep, D. et al., Bio/Technology, vol. 9, 1991, pp. 183–187.
Lamsa, Michael et al., Jrn. Of Indus. Microbio., vol. 5, 1990, pp. 229–238.
Ward, Michael et al., Bio/Technology, vol. 8, 1990, pp. 435–440.
Nyyssönen, Eini et al., Bio/Technology, vol. 11, 1993, pp. 591–595.

INCREASED PRODUCTION OF SECRETED PROTEINS BY RECOMBINANT YEAST CELLS

This application is the national phase under 35 U.S.C. §371 of PCT International Application No. PCT/FI98/00576 which has an International filing date of Jul. 8, 1998 which designated the United States of America.

FIELD OF THE INVENTION

This invention relates to recombinant-DNA-technology. Specifically this invention relates to new recombinant yeast cells transformed with SEB1 gene or its homologs. A yeast cell transformed with several copies of a SEB1 gene or a gene homologous to SEB1 has an increased capacity to produce secreted foreign or endogenous proteins.

Further, said new recombinant yeast cells, when transformed with genes expressing suitable hydrolytic enzymes can hydrolyze and/or utilize appropriate macromolecular/polymeric compounds more efficiently, which results in increased cell mass production and/or more versatile utilization of the compounds in relevant biotechnical applications.

BACKGROUND OF THE INVENTION

The development of recombinant DNA methods has made it possible to produce proteins in heterologous host systems. This possibility greatly facilitates production of e.g. proteins of therapeutic importance which normally occur in nature in very low amounts or are otherwise difficult to isolate or purify. Such proteins include growth factors, hormones and other biologically active proteins or peptides which traditionally have been isolated from human or animal tissues or body fluids e.g. blood serum or urine. The increasing danger of the presence of human pathogenic viruses such as HBV, HIV, and oncogenic viruses, prions, or other pathogens in the human or animal tissues or body fluids has greatly speeded up the search for heterologous production systems for these therapeutics. Other proteins of clinical importance are viral or other microbial or human parasite proteins needed for diagnostics and for vaccines especially of such organisms which are difficult to grow in vitro or in tissue culture, or are dangerous human pathogens. These include viruses like HBV, HIV, yellow fever, rubella, FMDV, rabies, and human parasites such as *Plasmodium falciparum* causing malaria.

A further group of proteins for which heterologous production systems have been or are being developed are secreted enzymes, especially those hydrolyzing plant material, and which are needed in food and fodder production as well as in other industrial processes including textile industry and pulp and paper industry. The possibility of producing proteins in heterologous systems or production of endogenous proteins in genetically engineered cells increases their yields and greatly facilitates their purification and has already by now had a great impact on studies of structure and function of many important enzymes and other proteins. The production and secretion of foreign hydrolytic enzymes in yeast for example, results in improvements in processes based on industrial yeast strains such as distiller's, brewer's or baker's yeasts.

Various production systems have been and are being developed including bacteria, yeasts, filamentous fungi, animal and plant cell cultures and even multicellular organisms like transgenic animals and plants. All of these different systems have their advantages, even if disadvantages, and all of them are needed.

The yeast *Saccharomyces cerevisiae* is at the moment the best known eukaryote at genetic level. Its whole genome sequence became public in data bases on Apr. 24, 1996. As a eukaryotic microbe it possesses the advantages of a eukaryotic cell like most if not all of the post-translational modifications of eukaryotes, and as a microbe it shares the easy handling and cultivation properties of bacteria. The large scale fermentation systems are well developed for *S. cerevisiae* which has a long history as a work horse of biotechnology including production of food ingredients and beverages such as beer and wine.

The yeast genetic methods are by far the best developed among eukaryotes based on the vast knowledge obtained by classical genetics. This made it easy to adopt and further develop for yeast the gene technology procedures first described for *Escherichia coli*. Along other lines the methods for constructing yeast strains producing foreign proteins have been developed to a great extent (Romanos et. al., 1992).

Secretion of the proteins into the culture medium involves transfer of the proteins through the various membrane enclosed compartments constituting the secretory pathway. First the proteins are translocated into the lumen of the endoplasmic reticulum, ER. From there on the proteins are transported in membrane vesicles to the Golgi complex and from Golgi to plasma membrane. The secretory process involves several steps in which vesicles containing the secreted proteins are pinched off from the donor membrane, targetted to and fused with the acceptor membrane. At each of these steps function of several different proteins are needed.

The yeast secretory pathway and a great number of genes involved in it have been elucidated by isolation of conditional lethal mutants deficient in certain steps of the secretory process (Novick et al., 1980; 1981). Mutation in a protein, needed for a particular transfer step results in accumulation of the secreted proteins in the preceding membrane compartment. Thus proteins can accumulate in the cytoplasm, at ER, Golgi or in vesicles between ER and Golgi, or in vesicles between Golgi and plasma membrane.

More detailed analysis of the genes and proteins involved in the secretory process has become possible upon cloning the genes and characterization of the function of their encoded proteins. A picture is emerging which indicates that in all steps several interacting proteins are functioning. The number of genes is rapidly increasing that are involved in protein secretion and that were first identified in and isolated from *S. cerevisiae* and were later found in other organisms including lower and higher eukaryotes. The structural and functional homology has been shown for many of such proteins.

We have recently cloned a new yeast gene, SEB1 (Toikkanen et al., 1996) which encodes the β-subunit of the trimeric Sec61 complex (hence the name: SEB=SEc61 Beta subunit) that is likely to represent the protein conducting channel of the ER both in co- and post-translational translocation (Hanein et al., 1996). In the former it functions in close connection with the ribosome and in latter it forms a heptameric membrane protein complex with the tetrameric Sec62/Sec63 complex (Panzner et al., 1995). Genes with sequence similarity to the SEB1 gene are found in plant and mammalian cells indicating that the Sec61 translocation complex is conserved in evolution. In fact, similar components function in protein translocation also in prokaryotes (discussed in Toikkanen et al., 1996). This further supports the conserved and central role of the SEB1 gene in protein secretion and intracellular transport. However, no reports exist so far on any positive effect of the SEB1 or its homologs in other yeasts, plant or animal cells on secretion when overexpressed, which effect we are showing in this invention for the yeast SEB1 gene. It should be noticed that Seb1 protein is present in a different protein complex and at different location than the Sso proteins which we have previously shown to enhance production of secreted proteins when present in the cells in higher than normal amounts.

Knowledge on the protein secretion process in *S. cerevisiae* is rapidly increasing. Less is known about the secretory system of other yeasts such as Kluyveromyces, Schizosaccharomyces, Pichia and Hansenula which, however, have proven useful hosts for production of foreign proteins (Buckholz and Gleeson, 1991; Romanos et al., 1992), or Candida and Yarrowia which also are interesting as host systems. The genetics and molecular biology of these yeasts are not as developed as for Saccharomyces but the advantages of these yeasts as production hosts are the same as for Saccharomyces.

Several attempts have been made and published previously to increase foreign protein production in yeast and filamentous fungi as well as in other organisms. Much work has been devoted to various promoter and plasmid constructions to increase the transcription level or plasmid copy number (see e.g. Baldari et al. 1987; Martegani et al. 1992; Irani and Kilgore, 1988). A common approach to try and increase secretion is to use yeast signal sequences (Baldari, et al. 1987, Vanoni et al. 1989). Random mutagenesis and screening for a secreted protein (Smith et al., 1985; Sakai et al., 1988; Shuster et al., 1989; Suzuki et al., 1989; Sleep et al., 1991; Lamsa and Bloebaum, 1990; Dunn-Coleman et al., 1991) or fusion of the foreign protein to an efficiently secreted endogenous protein (Ward et al., 1990; Harkki et al., 1989; Nyyssönen et al. 1993; Nyyssönen et al., 1992) have been widely used both for yeast and filamentous fungi in order to make the secretion of foreign proteins more efficient. Both of these methods are of limited use. Overproduction mutants isolated by random mutagenesis and screening are almost exclusively recessive and thus cannot be transferred into industrial yeast strains which are polyploid. Often the overproduction results from changes other than increased secretion and in many cases affects only the protein used for screening. Fusion protein approach requires tailoring of the fusion construction for each foreign protein separately. The fusion protein is often not functional and thus the final product must be released by proteolytic cleavage which complicates the production procedure.

Our approach, increasing the copy number of genes functioning in secretion and thus the amount of components of the secretory machinery is more universal: it is applicable to any protein without specific fusion constructions and applicable to diploid and polyploid strains.

It is not exactly known which steps form the bottle necks in the secretory process, but it can be anticipated that there are more than one stage that may become rate limiting especially under overproduction conditions. The SEB1 gene according to the invention was cloned using a yeast genetic approach and it was shown to interact genetically with the SEC61 gene, encoding the major component of the ER translocation complex. The fact that overexpression of SEB1 gene increases the production of secreted proteins into the culture medium suggests that the Seb1 protein is a rate limiting component in the translocation process. This was surprising since Seb1 protein is a component of a multiprotein complex and the enhancing effect did not require increased levels of the other components of the complex and since the SEB1 gene is not essential for yeast growth. This could mean that there is another gene which can perform the same function as SEB1. We have isolated another gene, SEB2, homologous to SEB1 but disruption of both SEB1 and SEB2 was not lethal either, indicating that the function of SEB1 is not essential for yeast growth.

SUMMARY OF THE INVENTION

The present invention describes a method for enhanced production of secreted proteins based on overexpression of the previously isolated SEB1 gene of *Saccharomyces cerevisiae*. Specifically, the present invention describes the construction of *S. cerevisiae* strains overexpressing the SEB1 gene either on a multicopy plasmid or when integrated into the yeast genome in single or multiple copies or placed under regulation of a strong promoter. In addition, this invention describes identification of SEB1 homologs from other yeasts, and detection of Seb1p homologous protein in *Kluyveromyces lactis*.

This invention thus provides new recombinant yeast cells expressing enhanced levels of Seb1 protein of *S. cerevisiae*.

This invention also provides process(es) for production of increased amounts of secreted proteins by overexpressing genes interacting with the SEB1 gene, such as SEC61.

The yeast cells according to the invention being transformed with the SEB1 gene or genes interacting with the SEB1 gene have an increased capacity to produce secreted proteins. The new yeast cells according to the invention can also be used for more efficient production of hydrolytic enzymes and hydrolysis of e.g. polymeric substrates which results in improvements in biotechnical processes such as single cell or baker's yeast production due to increased cell mass or in other processes where efficient production of hydrolytic enzymes and/or efficient hydrolysis of plant material is beneficial.

DETAILED DESCRIPTION OF THE INVENTION

For better understanding of the following detailed description of the invention the following definitions of certain terms are given to be used hereinafter.

Homologous genes, homologs: Genes which are related, but not identical, in their DNA sequence and/or perform the same function are homologous with each other and are called each other's homologs.

Overexpression of a gene: A protein encoded by said gene is produced in increased amounts in the cell. This can be achieved by increasing the copy number of the gene by introducing extra copies of the gene into the cell on a plasmid, or integrated into the genome. Overexpression can also be achieved by placing the gene under a promoter stronger than its own promoter. The amount of the protein in the cell can be varied by varying the copy number of the gene and/or the strength of the promoter used for the expression.

Secreted proteins: Proteins which inside of the cell are directed to the secretory pathway and transported through it to the exterior of the cell, outside of the plasma membrane, are called secreted proteins. In yeast the proteins may remain associated with the cell wall such as invertase or may be released through the cell wall into the growth medium such as the foreign protein Bacillus α-amylase.

Suppression of a mutation: When the effect of a mutation in a given gene is alleviated or abolished by a mutation in another gene, this second gene is called a suppressor of the first gene. Suppression can occur also by overexpression of the wild type allele of the second gene by the means described above. This is called overexpression suppression. If the overexpression is caused by multiple copies of the suppressing gene the suppression can also be called multicopy suppression. Suppression phenomenon indicates that these two genes interact at genetic level. The interaction may also occur at physical level as direct, physical contact between the two proteins encoded by the interacting genes.

Transformant/segregant: When yeast is transformed with a plasmid it is called transformant, i.e. a transformed strain. When the plasmid is lost, i.e. segregated away from the transformant the strain is called a segregant.

SEB1 gene to be used in this invention is isolated from an organism containing this gene, e.g. *Saccharomyces cerevisiae* or *Kluyveromyces lactis*. Also other suitable yeasts, such as *Schizosaccharomyces pombe, Yarrowia lipolytica,* Candida spp., Pichia spp. and Hansenula spp. can be used. It is to be noted that homologous genes from other organisms can also be used.

Furthermore, overexpression of other genes functioning at the same step with the SEB1 gene, such as SEC61, in the presence of normal or increased levels of Seb1 protein results in increased production of secreted proteins.

Genes functioning at the other steps of the secretory process may well have a similar effect. Thus, release of the secretory vesicles from ER or the Golgi compartment may be facilitated by increasing the copy number of appropriate genes known to function at this step or by searching for and increasing the copy number of genes interacting with the known genes, e.g. suppressors of their mutations. Likewise any other step of the secretory process may be improved by increasing the copy number of genes involved. The new gene SEB1, which we have isolated from *S. cerevisiae*, represents a conserved gene which suggests that it plays an important role in the cell.

Based on the conserved nature of SEB1 and its homologs in other species, as mentioned above, we propose that increase of the SEB1 gene or its homolog in any other yeasts would result in increased protein secretion efficiency.

The host to be transformed with the genes of the invention can be any yeast cell suitable for foreign or endogenous protein production, e.g. any *S. cerevisiae* yeast strain, (e.g. DBY746, AH22, S150-2B, GPY55-15Ba, VTT-A-63015) any *Kluyveromyces lactis* yeast (e.g. MW270-7B, MW179-1D), *Schizosaccharomyces pombe, Hansenula polymorpha,* Candida, Pichia or Yarrowia spp. Transfer of the genes into these cells can be achieved, for instance, by using the conventional methods described for these organisms.

The DNA sequence containing SEB1 is isolated from *S. cerevisiae* by conventional methods. In a preferred embodiment the known DNA sequence of the SEB1 gene of *S. cerevisiae* (Toikkanen et al., 1996) and SEB1-like genes is used to design probes for heterologous hybridization or PCR primers for cloning the SEB1 gene. In another approach antibodies to the proteins encoded by the known SEB1 and SEB1-like genes are used for cloning the gene by standard methods.

The DNA sequence of *K. lactis* containing the *K. lactis* SEB1 gene is isolated from the chromosomal DNA or from a cDNA or a chromosomal gene bank prepared from *K. lactis* by heterologous hybridization in non-stringent conditions as described in Example 5, and characterized by conventional methods, and its function can be shown as described above. Similar approach is suitable for all organisms which have shown to possess chromosomal sequences homologous to the yeast SEB1 gene as analyzed for instance by Southern hybridization of total DNA. It is also possible to isolate the gene from an expression library with antibodies prepared against the yeast Seb1 protein.

Alternatively, oligonucleotide primers can be designed based on the homologies found between the sequences of the corresponding genes isolated from several organisms. These primers are used to amplify the *K. lactis* gene in a PCR reaction.

To construct a plasmid suitable for transformation into a yeast, the SEB1 gene is cloned into a suitable yeast expression vector, such as pAAH5 (Ammerer, 1983) or vectors derived from it (Ruohonen et al., 1991; Ruohonen et al., 1995) comprising the appropriate yeast regulatory regions. These regulatory regions can be obtained from yeast genes such as the ADH1, GAL1/GAL10, PGK1, CUP1, GAP, CYC1, PHO5, TPI1 or asparagine synthetase gene, for instance. Alternatively, also the regulatory regions of SEB1 can be used to express the genes in *S. cerevisiae*. The plasmid carrying the SEB1 gene is capable of replicating autonomously when transformed into the recipient yeast strain. The gene SEB1 together with the appropriate yeast regulatory regions can also be cloned into a single copy yeast vector such as pHR70 of Hans Ronne or pRS313, pRS314, pRS315 or pRS316 (Sikorski and Hieter, 1989).

Figure 6:
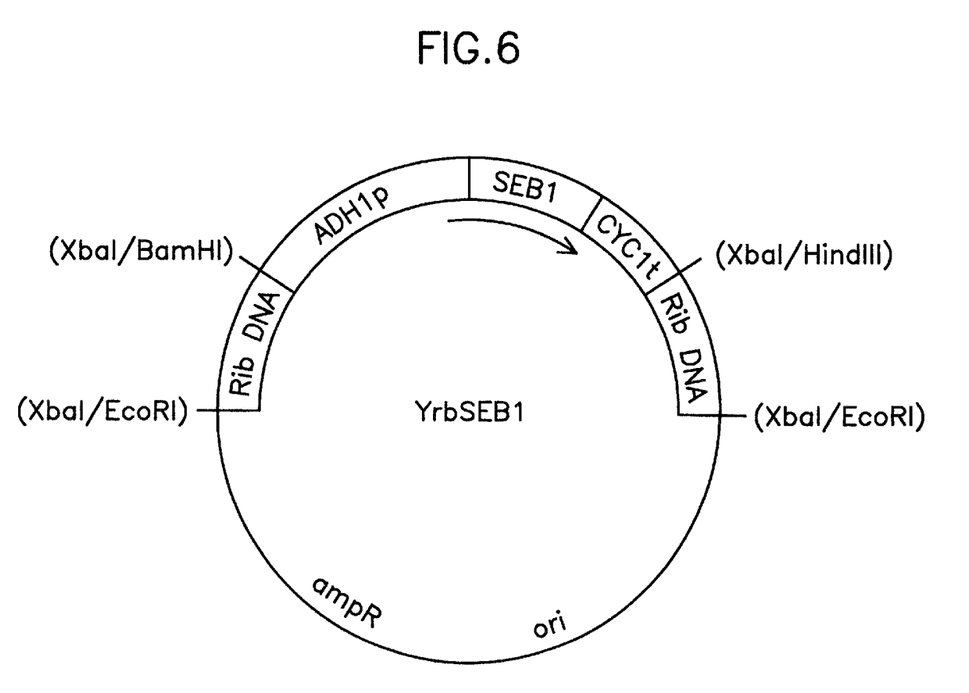
FIG. 6 shows the SEB1 expression cassette flanked by ribosomal sequences integrated into BS+, generating the vector YrbSEB1.

Alternatively, extra copies of SEB1 gene can also be integrated into the yeast chromosome, into the ribosomal RNA locus, for instance. For this purpose the ribosomal sequences of a suitable plasmid, e.g. plasmid pIRL9 (Hallborn et al., 1991) are released, and cloned appropriately into BS+ vector, as shown in FIG. 6. The gene SEB1 coupled in between suitable yeast promoter and terminator regions, is released from the hybrid vector comprising the gene and cloned into the plasmid obtained at the previous stage. From this resulting plasmid the expression cassette, flanked by ribosomal sequences can be released. This fragment is cotransformed into a yeast with an autonomously replicating plasmid carrying a suitable marker for transformation. The plasmid can be later on removed from the cells containing the extra copies of SEB1 gene integrated in the chromosome by cultivating the cells in non-selective conditions. Using this procedure recombinant strains can be obtained which carry no extra foreign DNA such as bacterial vector sequences. If a polyploid yeast strain, such as VTT-A-63015, is used the gene can be integrated also to an essential locus such as the ADH1 or the PGK1 locus.

To express the SEB1 gene in *K. lactis* the SEB1 gene between the ADH1 promoter and CYC1 terminator is transformed into a *K. lactis* strain either on a multicopy plasmid or integrated in the genome using methods known in the art. Suitable promoters in addition to the ADH1 promoter or promoter of the SEB1 gene itself are for instance the other *S. cerevisiae* promoters, as listed hereinbefore.

An object of this invention is thus to provide yeast strains overexpressing the SEB1 gene of *S. cerevisiae* as well as homologous gene(s) of *K. lactis* and other yeasts. The sequence of the genes can be determined from the plasmids carrying them by using e.g. the double stranded dideoxy nucleotide sequencing method (Zagursky et al., 1986). The nucleotide sequence of the open reading frame of SEB1 gene of *S. cerevisiae* is given as the SEQ ID NO:1.

Another object of this invention is to provide specific vectors comprising the SEB1 genes. For yeast such a vector is either an autonomously replicating multicopy or a single copy plasmid or a vector capable of integrating into the chromosome, as described above.

Still another object of this invention is to provide yeast strains containing extra copies of SEB1 gene either on replicating plasmid(s) or integrated into the chromosome, which results in increased production of secreted proteins, such as Bacillus α-amylase, yeast invertase or Trichoderma cellulases or other hydrolases.

Thus a method for constructing new yeast cells capable of expressing enhanced levels of Seb1 protein comprises:

(a) obtaining a vector comprising an isolated DNA molecule encoding Seb1 protein; and (b) transforming at least one such vector to a yeast host cell.

Still another object of this invention is to provide yeast cells which in addition to extra copies of SEB1 gene comprise a DNA molecule encoding a secreted foreign or endogenous protein, such as α-amylase, cellulase, or an antibody, and are capable of expressing this protein.

Thus a process for producing increased amounts of a secreted foreign or endogenous protein by overexpressing the SEB1 gene is provided. This process comprises:

(a) obtaining a vector comprising an isolated DNA molecule encoding said protein;

(b1) transforming the vector obtained into a suitable yeast host expressing enhanced levels of Seb1 protein to obtain recombinant host cells; or (b2) transforming the vector obtained into a suitable yeast host and retransforming this transformant with SEB1 or a gene homologous to SEB1;

(c) screening for cells with enhanced production of said protein; and (d) cultivating said recombinant host cells under conditions permitting expression of said protein.

A further object of this invention is to improve secretion by optimizing the Seb1 protein level using different promoters and different copy numbers of the gene and combining the SEB1 gene with other genes involved in secretion, such as SEC61.

Thus the invention provides a process for producing increased amounts of a secreted foreign or endogenous protein, by overexpressing a gene interacting with the SEB1 gene, e.g. SEC61, in the presence of normal or increased amounts of the Seb1 protein, which process comprises:

(a) obtaining a vector comprising an isolated DNA molecule encoding said protein;

(b1) transforming the vector obtained into a suitable yeast host expressing normal or enhanced levels of Seb1 protein and overexpressing another gene interacting with SEB1 gene, e.g. SEC61, to obtain recombinant host cells; or, (b2) transforming the vector into a suitable yeast host and retransforming this transformant with SEB1 or a gene homologous to SEB1 and by the gene interacting with SEB1 gene;

(c) screening for cells with enhanced production of said protein; and (d) cultivating said recombinant host cells under conditions permitting expression of said protein.

Still another object of this invention is to provide a process for increased production of an endogenous secreted protein, the process comprising:

(a) transforming cells producing said protein with a SEB1 gene or a gene homologous to SEB1, alone or together with a gene interacting with the SEB1 gene, such as SEC61, (b) screening for transformants producing enhanced level of said protein thus obtaining recombinant cells for enhanced protein production, and (c) cultivating said recombinant cells in conditions permitting expression of said protein.

Still another object of this invention is to provide yeast strains which in addition to extra copies of SEB1 gene or its homolog comprise a DNA sequence coding for a hydrolytic enzyme such as α-amylase and/or glucoamylase or lignocellulose hydrolyzing enzymes such as cellulases, hemicellulases or ligninases, which render the yeast capable of increased hydrolysis of, and/or enhanced growth on polymeric compounds such as starch or lignocellulose.

Thus an efficient biomass production on said raw material or efficient hydrolysis of said raw material is provided. This process comprises:

(a) obtaining a yeast vector comprising an isolated DNA molecule encoding an endogenous or foreign hydrolytic enzyme;

(b1) transforming the vector obtained into a suitable yeast host expressing enhanced levels of Seb1 protein to obtain recombinant yeast host cells; or (b2) transforming the vector to a suitable yeast host and retransforming this transformant with SEB1 or a gene homologous to SEB1;

(c) screening for cells with enhanced production of said enzyme; and (d) cultivating said recombinant host cells under conditions permitting expression of said hydrolytic enzyme.

A process is also provided for efficient biomass production on a raw material or efficient hydrolysis of a raw material, by overexpressing genes interacting with the SEB1 gene, e.g. SEC61, in the presence of normal or increased amounts of the Seb1 protein. This process comprises:

(a) obtaining a vector comprising an isolated DNA molecule encoding an endogenous or foreign hydrolytic enzyme;

(b1) transforming the vector obtained to a suitable yeast host expressing enhanced levels of a protein interacting with the Seb1 protein in the presence of normal or increased amounts of the Seb1 protein to obtain recombinant yeast host cells; or, (b2) transforming the vector to a suitable yeast host and retransforming this transformant with SEB1 gene or a gene homologous to SEB1 and with a gene interacting with SEB1 gene, such as SEC61;

(c) screening for cells with enhanced production of said enzyme; and (d) cultivating said recombinant yeast host cells under conditions permitting expression of said hydrolytic enzyme.

Possible applications of said recombinant cells are e.g. in single cell production, in improved alcohol production or in processes where efficient hydrolysis of raw material is desired.

Experimental

The *S. cerevisiae* strain used in all experiments was DBY746 (a his3D1 leu2–3 leu2–112 ura3–52 trp1–289 $Cyh^R$) (obtained from David Botstein, Department of Biology, Massachusetts Institute of Technology, Cambridge, Mass.)

EXAMPLE 1

Overexpression of the Seb1 Protein in Yeast Transformed with YEpSEB1

Figure 1:
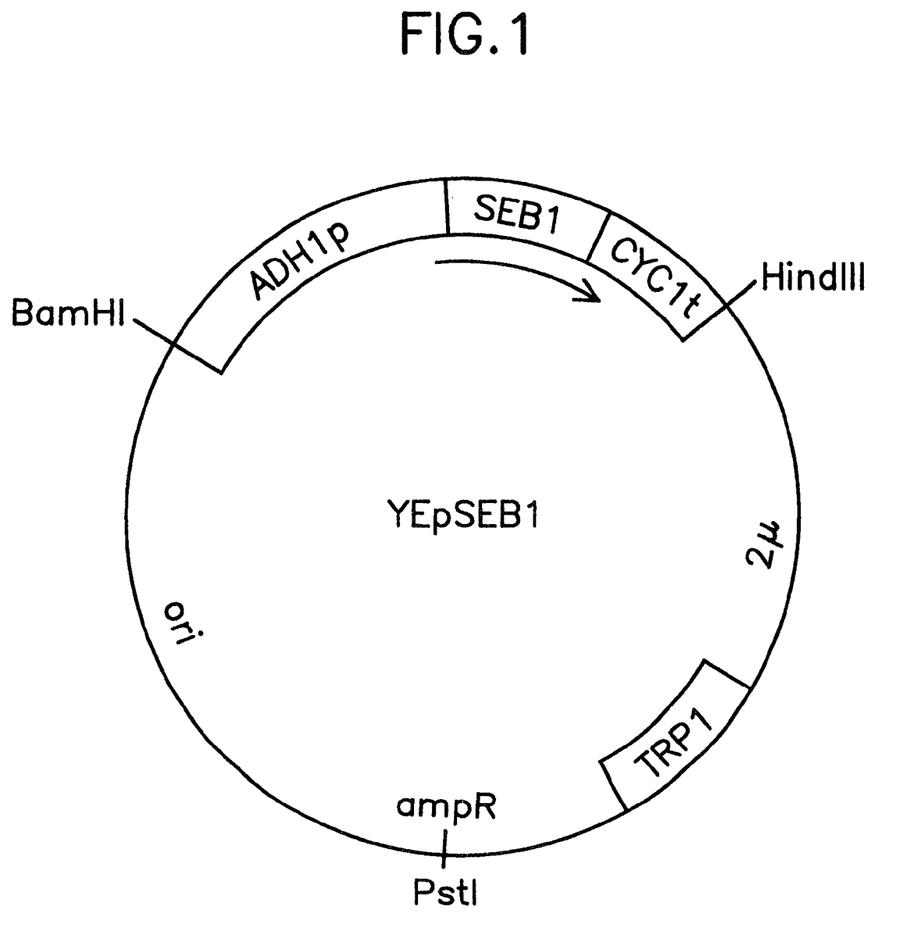
FIG. 1 shows the *S. cerevisiae* vector YEpSEB1 in which the SEB1 gene cDNA is integrated between the ADH1 promoter and CYC1 terminator on the multicopy plasmid pMAC561.
Figure 2:
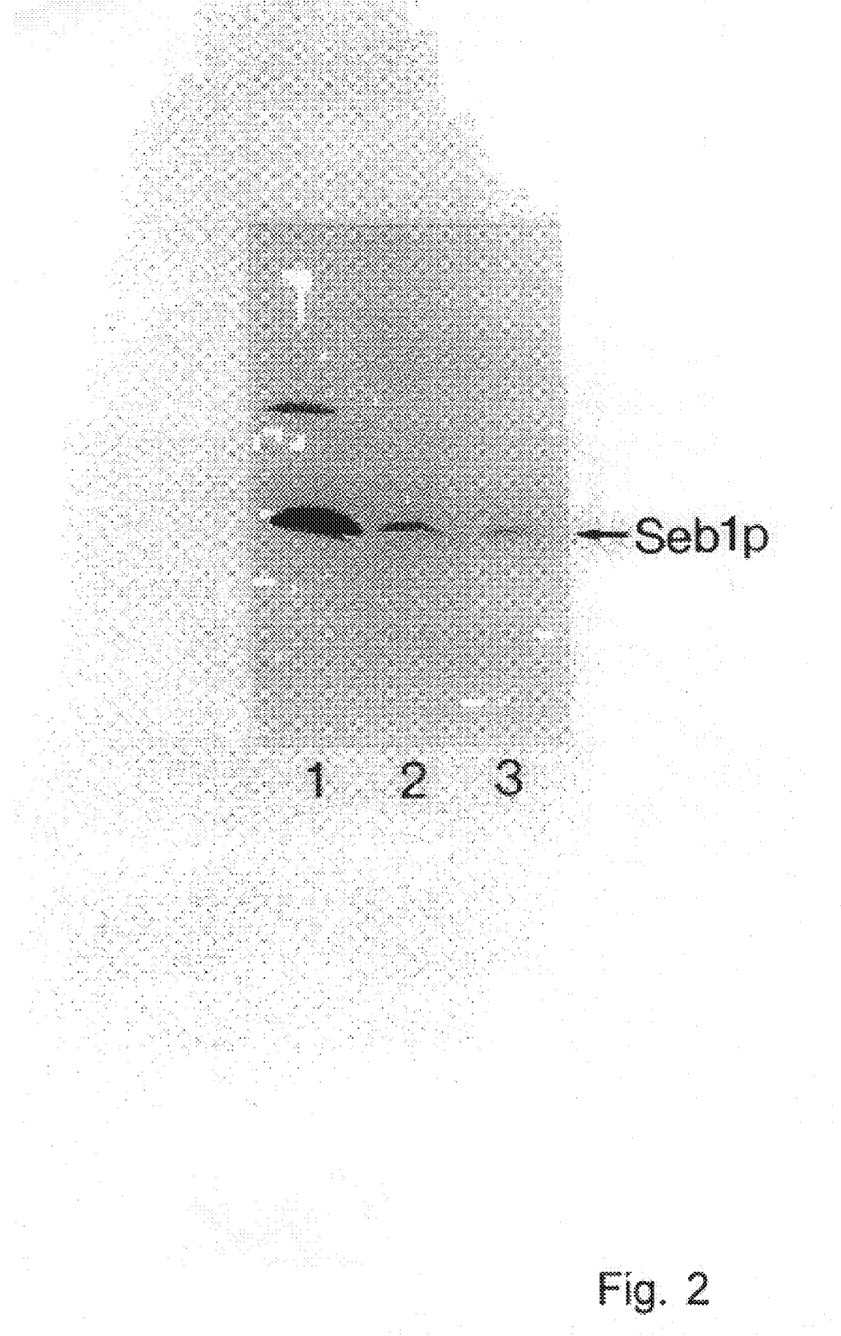
FIG. 2 shows Western analysis demonstrating overexpression of Seb1 protein in yeast transformed with YEpSEB1. Lane 1: SEB1 overexpression strain transformed with plasmid YEpSEB1, Lane 2: Trp$^-$ segregant of SEB1 overexpression strain, Lane 3: Control strain (with plasmid pMA56).

The *S. cerevisiae* strains transformed (Ito et al., 1983) with the control plasmid pMA56 (1) (Ammerer, 1983) or with YEpSEB1 (3) (Toikkanen et al., 1996) were grown in synthetic complete medium (Sherman et al., 1983) lacking Trp, and a strain from which the YEpSEB1 plasmid was segregated away (2) was grown in synthetic complete medium. Yeast cell lysates were prepared in the presence of SDS as described by Keränen (1986). Thirty µg of total yeast protein present in the lysates were separated by SDS-PAGE (Schägger and von Jagow, 1987) and detected by Western blotting using polyclonal antibodies made in rabbit against an 18 amino acids long N-terminal peptide of the Seb1 protein (Toikkanen et al., 1996) and alkaline phosphatase conjugated goat anti-rabbit IgG for detection. As shown in FIG. 2, greatly increased amount of Seb1 protein was seen in the YEpSEB1 transformant. When the YEpSEB1 plasmid was segregated away from the yeast, the Seb1 protein level was reduced to the level of the control strain transformed with the vector plasmid not containing the SEB1 gene.

EXAMPLE 2

Enhanced Production of a Secreted Foreign Protein, Bacillus α-Amylase and an Endogenous Protein, Invertase in a Yeast Strain overexpressing SEB1

Figure 3:
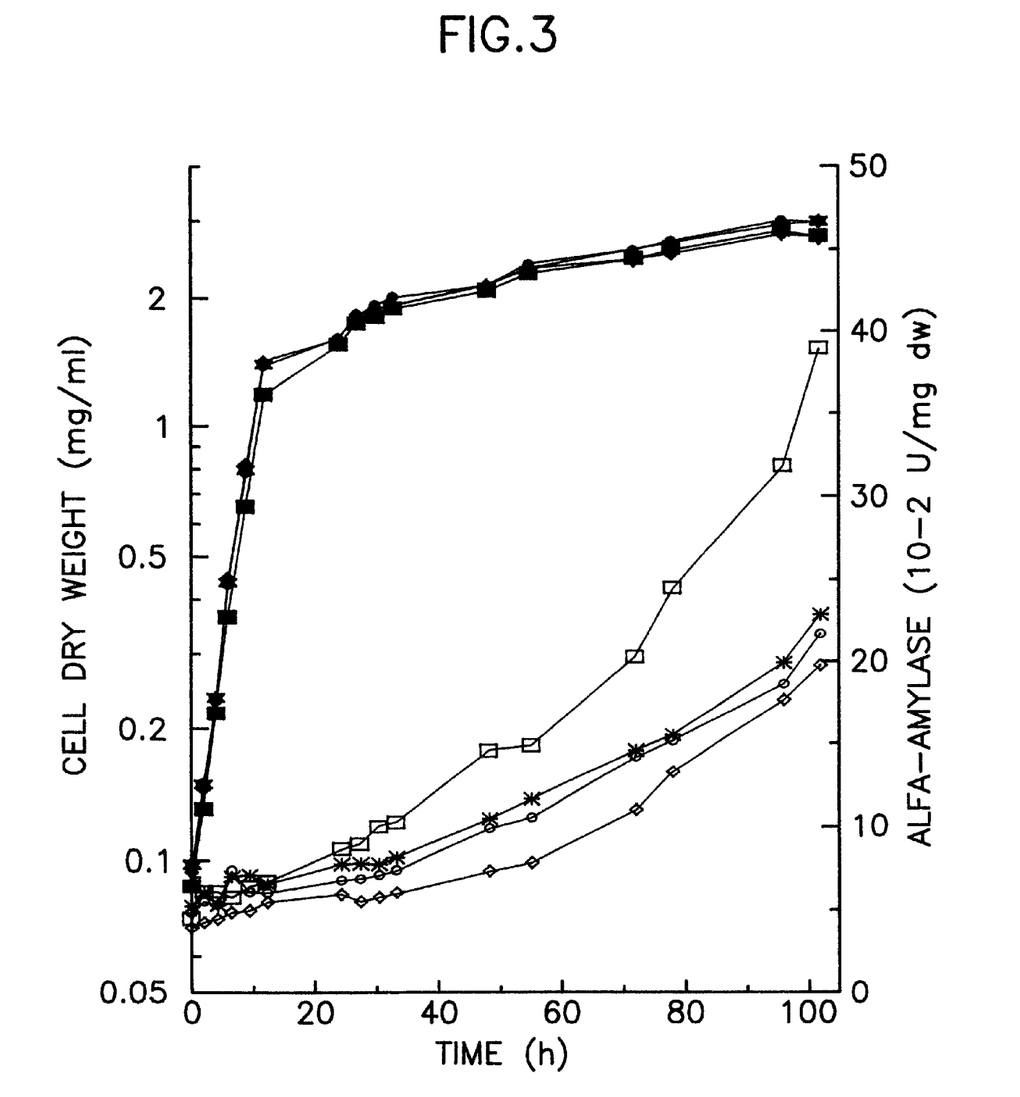
FIG. 3 shows increased production of secreted Bacillus α-amylase by *S. cerevisiae* transformed with the multicopy plasmid YEpSEB1 expressing SEB1 and with YEpαa6 expressing Bacillus α-amylase gene. Growth (filled symbols) and secretion of α-amylase (open symbols) in the yeast transformant overexpressing the SEB1 gene (YEpαa6 and YEpSEB1; squares), in control transformant (YEpαa6 and pMA56; diamonds), in YEpSEB1 segregant (YEpαa6; circles) and in α-amylase transformant (YEpαa6; stars).

The *S. cerevisiae* strain harboring the plasmid YEpαa6 containing Bacillus α-amylase gene ligated between the ADH1 promoter and terminator (Ruohonen et al., 1987), modified for more efficient expression by deleting predicted inhibitory sequences 5' to the promoter element (Ruohonen et al., 1991; 1995) was transformed either with YEpSEB1 or with the control plasmid pMA56 (Ammerer, 1983). The yeast strains obtained containing YEpSEB1 and YEpαa6 or pMA56 and YEpαa6 were grown in selective medium at 30° C. and secretion of α-amylase into the culture medium was monitored by measuring the α-amylase activity using the Phadebas amylase test (Pharmacia Diagnostics AB, Sweden). As shown in FIG. 3, increased α-amylase activity was obtained in the strain which carried SEB1 on the multicopy plasmid compared with the control strain transformed with the control plasmid without SEB1 gene. No difference was observed in the yeast growth between the control transformant and SEB1 transformant. Secretion of the endogenous protein, invertase, was also enhanced by SEB1 overexpression measured at late logarithmic to early stationary growth phase. The secreted invertase activity in the YEpSEB1 transformant was 1.4 fold compared to that of the control transformant containing pMA56.

Removal of the predicted inhibitory sequences on the ADH1 promoter (see above) used for expression of the SEB1 in YEpSEB1 results in prolonged expression of SEB1 and prolongs existence of increased level of the Seb1 protein and consequently even higher final levels of the Bacillus α-amylase are secreted into the medium.

EXAMPLE 3

Enhanced Production of Secreted Foreign Protein, Bacillus α-amylase in a Yeast Strain in which the α-amylase Gene is Integrated in the Genome at HIS3 Locus and the SEB1 Gene is Overexpressed The cassette expressing α-amylase of *Bacillus amyloliquefaciens* was released from the plasmid YEpαa6 (Ruohonen et al., 1995) as 3.35 kb fragment by digesting with BamHI and SalI and it was cloned into the yeast integrating vector pRS403 (Sikorski and Hieter, 1989) between the BamHI and SalI sites to obtain plasmid YIpαa1. The plasmid was linearized by PstI digestion inside the HIS3 gene and used for transformation of yeast. The transformants were selected for histidine prototrophy. Integration of the α-amylase expression cassette at the HIS3 locus was confirmed by Southern analysis. The integrant strain thus obtained was transformed with YEpSEB1 or with the control plasmid pMA56. The transformants were grown in selective medium at 30° C. and secretion of α-amylase into the culture medium was monitored by measuring the α-amylase activity as described in Example 2. Clearly enhanced levels of secreted α-amylase were detected in the YEpSEB1 transformant, in which the α-amylase level in the culture medium was 4.2 fold compared to the control strain.

EXAMPLE 4

Enhanced Production of Secreted Foreign Protein, Bacillus α-amylase in a Yeast Strain in which the α-amylase Gene is Integrated in the Genome at URA3 Locus and the SEB1 Gene is Overexpressed An integration cassette for integration of the α-amylase gene in the URA3 locus was constructed as follows. Two URA3 fragments were made by PCR and cloned into the multiple cloning site of pBluescript SK(−). The first fragment comprising base pairs (bp) 71–450 of the 1135 bp long URA3 was cloned as a SacI-XbaI fragment. The second fragment (781–1135 bp) was cloned as a XhoI-KpnI fragment. The resultant plasmid is pBUF. The 3.35 kb long α-amylase expression cassette was cut as a BamHI-SalI fragment from the plasmid YEp60 a6 (Ruohonen et al., 1995) and cloned into the pBluescript vector yielding plasmid pBαa6. The expression cassette was then released again as a BamHI-SalI fragment and inserted into pBUF between the URA3 fagments. This construct is pUIαa1. The *S. cerevisiae* strain which is ura3–52 was first converted to wt URA3 by transforming with a fragment containing the entire URA3 gene. This strain was then transformed with the α-amylase integration cassette released as a SacI-NsiI fragment from pUIαa1 and the transformants were selected in the presence of 5-FOA which selects for strains in which the URA3 gene is inactivated by integration of the α-amylase cassette. Integration at the URA3 locus was confirmed by Southern analysis. The strain thus obtained was transformed with YEpSEB1 or with the control plasmid pMA56. The YEpSEB1 transformant obtained was named VIT C-97280 and was deposited according to the Budapest Treaty at DSMZ (Deutsche Sammlung von Mikroorganismen und Zellkulturen GmbH) on Jun. 16, 1997 with the accession number DSM 11615.

Figure 4:
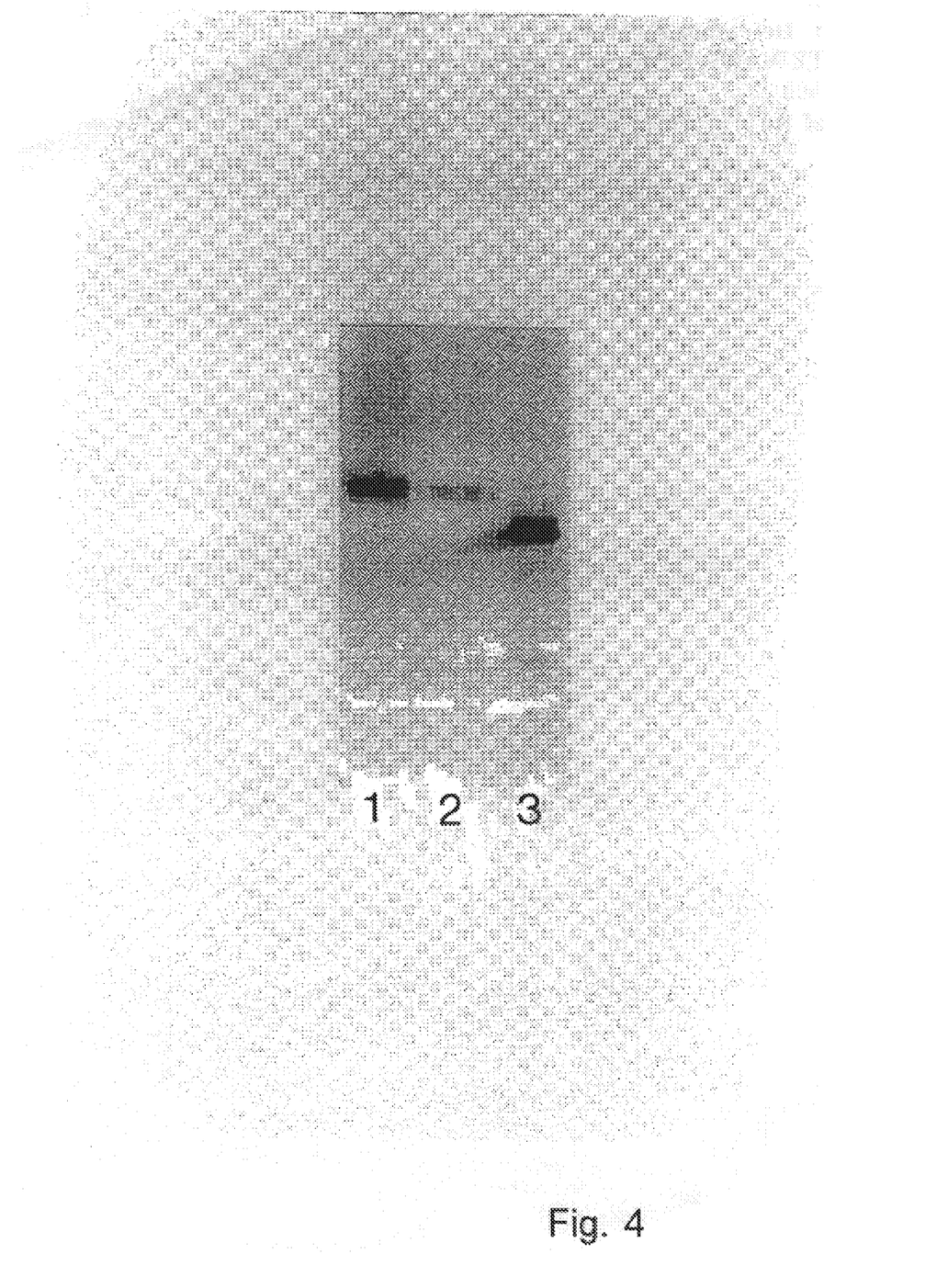
FIG. 4 shows Western analysis of Bacillus α-amylase secreted by *S. cerevisiae* with or without the multicopy plasmid expressing SEB1. Lane 1: Culture medium from YEpSEB1 transformant, Lane 2: Culture medium from control strain, Lane 3: Bacillus α-amylase standard.
Figure 5:
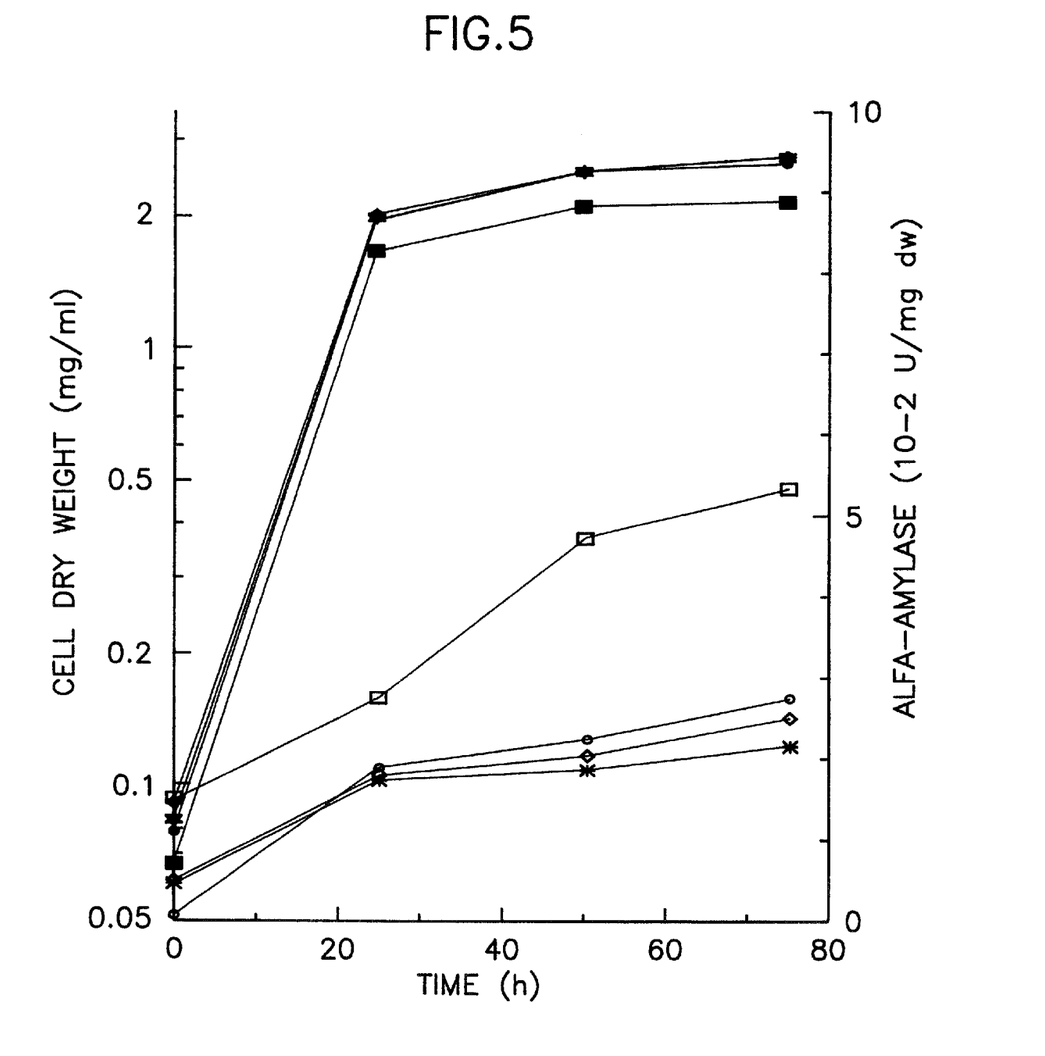
FIG. 5 shows increased production of secreted Bacillus α-amylase by *S. cerevisiae* strain containing an integrated copy of a Bacillus α-amylase gene and transformed with multicopy plasmid, expressing SEB1 gene. The secretion of Bacillus α-amylase integrant yeast (open symbols); the transformant overexpressing the SEB1 gene (YEpSEB1; squares), control transformant (pMA56, circles), YEpSEB1 segregant (diamonds) and pMA56 segregant (stars). The growth of the yeast transformants is shown with filled symbols.

The transformants were grown in selective medium at 30° C. and secretion of α-amylase into the culture medium was monitored by measuring the α-amylase activity as described in Example 2. As shown in FIG. 4 and FIG. 5 clearly enhanced levels of secreted α-amylase were detected in the YEpSEB1 transformant both by Western blotting and by measuring the α-amylase activity.

Figure 7:
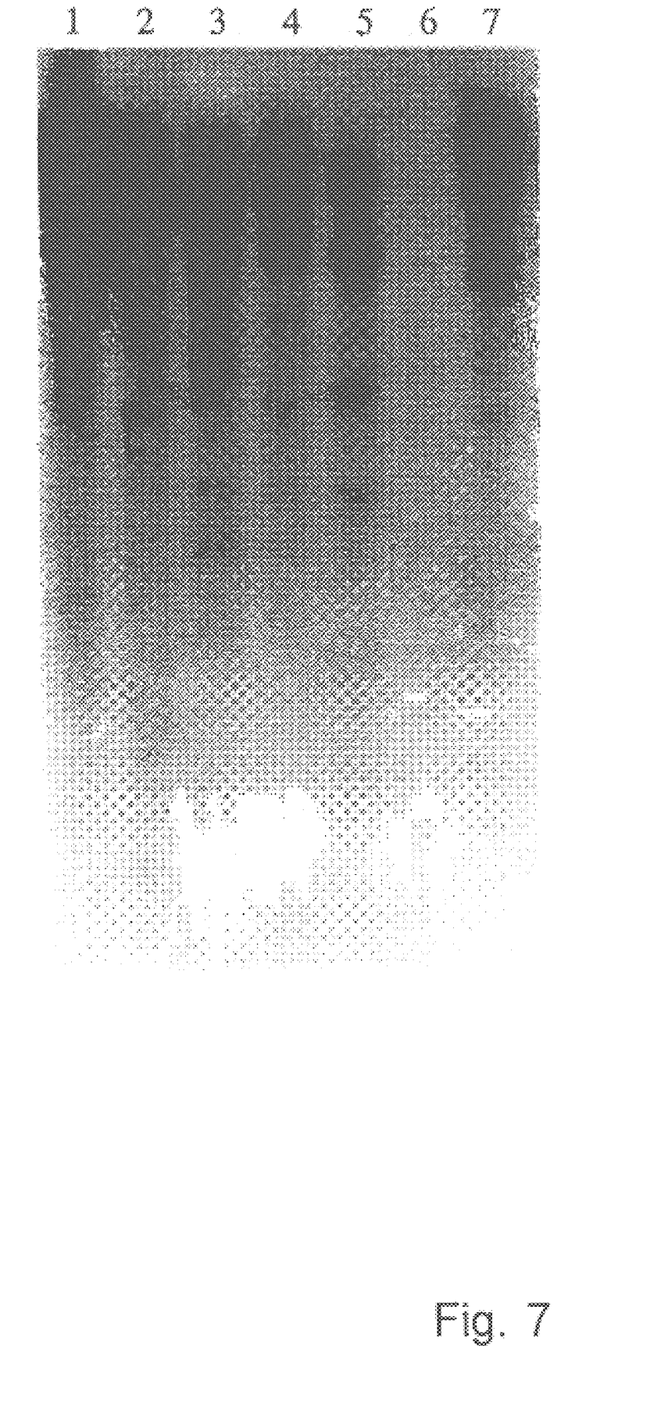
FIG. 7 Identification of SEB1 homologs in other yeast species by heterologous hybridization under non-stringent conditions. HindIII digested genomic DNA of *Saccharomyces cerevisiae* (lane 1), *Schizosaccharomyces pombe* (lane 2), *Kluyveromyces lactis* (lane 3), *Pichia pastoris* (lane 4), *Pichia stipitis* (lane 5), *Candida utilis* (lane 6) and *Yarrowia lipolytica* (lane 7).

EXAMPLE 5
Identification of SEB1 Homologs in other Yeasts by Heterologous Hybridization Genomic DNA from the fungal species *Saccharomyces cerevisiae, Schizosaccharomyces pombe, Kluyveromyces lactis, Pichia pastoris, Pichia stipitis, Candida utilis,* and *Yarrowia lipolytica* were isolated, digested with the HindIII restriction enzyme, separated electrophoretically in an 0.8% agarose gel and blotted on a nylon filter. Southern hybridization of the filter was carried out at different stringencies using the Saccharomyces SEB1 gene coding region as a probe. Hybridization in a mixture containing 30% formamide, 6×SSC, 10×Denhardt's, 0.5% SDS, 100 mg/ml herring sperm DNA and 10 mg/ml polyA at 35° C. and washing 15 minutes in 6×SSC, 0.1% SDS at 42° C. and 2×30 minutes in 2×SSC, 0.1% SDS at 42° C. revealed clear hybridizing bands in DNA derived from *S. cerevisiae, S. pombe, K. lactis, P. stipitis* and *Y. lipolytica*, and a much weaker band in DNA of *C. utilis* (FIG. 7).

Figure 8:
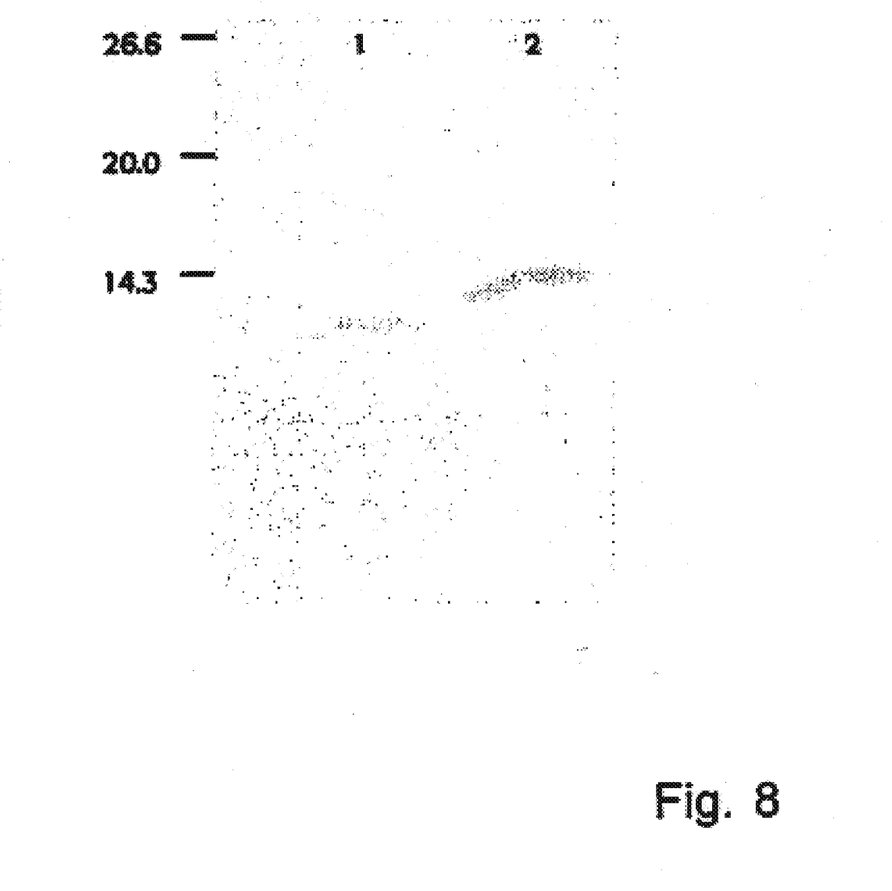
FIG. 8 Detection of the Seb1p and its homolog in *K. lactis* yeast using Seb1p specific antibody. *S. cerevisiae* (lane 1), *K lactis* (lane 2).

EXAMPLE 6
Detection of Seb1p Homologous Protein in *Kluyveromyces Lactis* Yeast The plasmid YEpSEB1 (*S. cerevisiae* vector containing SEB1 gene) and the vector plasmid were converted to shuttle vectors that are able to replicate in *K. lactis*. The *K. lactis* replication origin (Chen et al., 1986) was released from the KEp6 plasmid as about 1000 bp fragment (digestion with AatII and ClaI, fill-in by T4 DNA polymerase) and purified and ligated in the PvuII site of YEpSEB1 and the vector control, pMA56 to obtain plasmids KEpSEB1 and KpMA56, respectively. The plasmids were transformed into *K. lactis* and the transformants were selected for growth on SC-Trp plates. SDS lysates prepared from the transformants were analyzed by Western blotting using Seb1p specific antibody as described in Example 1. The antibody detected a band with slightly slower migration than that of Seb1p of *S. cerevisiae* (FIG. 8).

EXAMPLE 7
Enhanced Production of Secreted Foreign Protein, Bacillus α-amylase in Yeast Overexpressing SEC61 in Combination with Normal or Increased Levels of Functional Seb1 Protein.

The *S. cerevisiae* strain in which the Bacillus α-amylase expression cassette is integrated at the URA3 locus was transformed either with a multicopy plasmid YEpSEC61 expressing the SEC61 gene or with the control plasmid pRS425 (Christianson et al., 1992). The transformants were grown in selective medium at 30° C. and secretion of α-amylase into the culture medium was monitored by measuring the α-amylase activity using the Phadebas amylase test (Pharmacia Diagnostics AB, Sweden). Increased α-amylase activity (1.3 fold) was obtained in the strain which carries SEC61 on a multicopy plasmid compared with the strain transformed with the vector without SEC61 gene.

Simultaneous overexpression of both Sec61p and Seb1p from two different plasmids enhanced production of secreted α-amylase even further (3.3 fold). Under these 2-plasmid conditions enhancement by SEB1 alone was 2.4 fold. The plasmid expressing the SEC61 gene is available at VTT, Biotechnical Laboratory, Espoo, Finland.

Deposited Microorganism

The following microorganism was deposited according to the Budapest Treaty at the Deutsche Sammlung von Mikroorganismen und Zellkulturen GmbH (DSMZ), Mascheroder Weg 1b, D-38124 Braunschweig, Germany.

| Strain | Accession number | Deposit date |
|---|---|---|
| *Saccharomyces cerecisiae* VTT C-97280 carrying the integrated α-amylase gene and plasmid YEpSEB1 | DSM 11615 | 16.06.1997 |

REFERENCES

Aalto, M. K., Ronne, H. and Keränen, S. 1993. Yeast syntaxins Sso1p and Sso2p belong to a family of membrane proteins that function in vesicular transport. EMBO J. 12, 4095–4104.

Ammerer, G. 1983. Expression of genes in yeast using the ADC1 promoter. Methods Enzymol. 101, 192–201.

Baldari, C., Murray, J. A. H., Ghiara, P., Cesareni, G. and Galeotti, C. L. 1987. A novel peptide leader which allows efficient secretion of a fragment of human interleukin 1b in *Saccharomyces cerevisiae*. EMBO J., 6, 229–234.

Buckholz, R. G. and Gleeson, M. A. 1991. Yeast systems for the commercial production of heterologous proteins. Bio/Technology 9, 1067–1072.

Chen, X. J., Saliola, M., Falcone, C., Bianchi, M. M. and Fukuhara, H. 1986. Sequence organization of the circular plasmid pKD1 from the yeast *Kluyveromyces drosophilarum*. Nucleic Acids Res. 14, 4471–4481.

Christianson, T. W., Sikorski, R. S., Dante, M., Shero, J. H. and Hieter, P. 1992. Multifunctional yeast high-copy-number shuttle vectors. Gene 110, 119–122.

Dunn-Coleman, N., Bloebaum, P., Berka, R., Bodie, E., Robinson, N., Armstrong, G., Ward, M., Przetak, M., Carter, G., LaCost, R., Wilson, L., Kodama, K., Baliu, E., Bower, B., Lamsa, M. and Heinsohn, H. 1991. Commercial levels of chymosin production by Aspergillus. Bio/Technology 9: 976–981.

Hallborn, J., Penttilä, M., Ojamo, H., Keränen, S. & Hahn-H ägerdal, B. 1991. Xylose utilization by recombinant yeasts. International Pat. Appl. WO 91/15588.

Hanein, D., Matlack, K. E. S., Jungnickel, B., Plath, K., Kalies, K-U., Miller, K. R., Rapoport, T. A. & Akey, C. W., 1996. Oligomeric rings of the Sec61 complex induced by ligands required for protein translocation. Cell 87, 721–732.

Harkki, A., Uusitalo, J., Bailey, M., Penttilä, M. & Knowles, J. K. C. 1989. A novel fungal expression system: secretion of active calf chymosin from the filamentous fungus *Trichoderma reesei*. Bio/Technology 7: 596–603.

Irani, M. H. and Kilgore, T. L. 1988. High level expression in yeast. European patent application EP 0 284 044 A1.

Ito, H., Fukuda, Y., Murata, K. and Kimura, A. 1983. Transformation of intact yeast cells with alkali cations. J. Bacteriol. 153, 163–168.

Keränen, S. 1986. Synthesis and processing of Semliki forest virus polyprotein in *Saccharomyces cerevisiae*: a yeast type glycosylation of E1 envelope protein. Gene 48, 267–275.

Lamsa, M. and Bloebaum, P. 1990. Mutation and screening to increase chymosin yield in a genetically-engineered strain of *Aspergillus awamori*. J. Ind. Microbiol. 5, 229–238.

Martegani, E., Forlani, N., Mauri, I., Porro, D., Schleuning, W. D. and Alberghina, L. 1992. Expression of high levels of human tissue plasminogen activator in yeast under the control of an inducible GAL promoter. Appl. Microbiol. Biotechnol, 37, 604–608.

Novick, P., Ferro, S. and Scheckman, R. 1981. Order of events in the yeast secretory pathway. Cell 25, 461–469.

Novick, P., Fields, C. and Scheckman, R. 1980. Identification of 23 complementation groups required for post-translational events in the yeast secretory pathway. Cell 21, 205–215.

Nyyssönen, E., Keränen, S., Penttilä, M., Takkinen, K. and Knowles, J. K. C. 1992. Immunoglobulin production by Trichoderma. International Pat. Appl. WO 92/01797.

Nyyssönen, E., Penttilä, M., Harkki, A., Saloheimo, A., Knowles, J. K. C. and Keränen, S. 1993. Efficient production of antibodies by the filamentous fungus *Trichoderma reesei*. Bio/Technology 11, 591–595.

Panzner, S., Dreier, L., Hartmann, E., Kostka, S. and Rapoport, T. A. 1995. Post-translational protein transport in yeast reconstituted with purified complex of Sec proteins and Kar2p. Cell 81, 561–570.

Romanos, M. A., Scorer, C. A. and Clare, J. J. 1992. Foreign gene expression in yeast: a Review. Yeast 8, 423–488.

Ruohonen, L., Aalto, M. K. and Keränen, S. 1995. Modifications to the ADH1 promoter of *Saccharomyces cerevisiae* for efficient production of heterologous proteins. J. Biotechnol. 39, 193–203.

Ruohonen, L., Hackman, P., Lehtovaara, P., Knowles, J. K. C. and Keränen, S. 1987. Efficient secretion of *Bacillus amyloliquefaciens* α-amylase by its own signal peptide in *Saccharomyces cerevisiae* host cells. Gene 59, 161–170.

Ruohonen, L., Penttilä, M. and Keränen, S. 1991. Optimization of Bacillus α-amylase production by *Saccharomyces cerevisiae*. Yeast 7, 337–346.

Sakai, A. Shimizu, Y. and Hishinuma, F. 1988. Isolation and characterization of mutants which show an oversecretion phenotype in *Saccharomyces cerevisiae*. Genetics 119, 499–506.

Schägger, H. and von Jagow, G. 1987. Tricine-sodium dodecyl sulphate polyacryl amide gel electrophoresis for the separation of proteins in the range from 1 to 100 kDa. Anal. Biochem. 166, 368–379.

Shuster, J. R., Moyer, D. L., Lee, H., Dennis, A., Smith, B. and Merryweather, J. P. 1989. Yeast mutants conferring resistance to toxic effects of cloned human insulin-like growth factor I. Gene 83, 47–55.

Sherman, F., Fink, G. and Hicks, J. B. 1983. Methods in Yeast Genetics. A Laboratory Manual. Cold Spring Harbor Laboratory Press, Cold Spring Harbor, N.Y.

Sikorski, R. S. and Hieter, P. 1989. A system of shuttle vectors and yeast host strains designed for efficient manipulation of DNA in *Saccharomyces cerevisiae*. Genetics 122, 19–27.

Sleep, D., Belfield, G. P., Ballance, D. J., Steven, J., Jones, S. Evans, L. R., Moir, P. D. and Goodey, A. R. 1991. *Saccharomyces cerevisiae* strains that overexpress heterologous proteins. Bio/Technology 9, 183–187.

Smith, R. A., Duncan, M. J. and Moir, D. T. 1985. Heterologous protein secretion from yeast. Science 229, 1219–1224.

Suzuki, K., Ichikawa, K. and Jigami, Y. 1989. Yeast mutants with enhanced ability to secrete human lysozyme: Isolation and identification of a protease-deficient mutant. Mol. Gen. Genet. 219, 58–64.

Toikkanen, J., Gatti, E., Takei, K., Saloheimo, M., Olkkonen, V., Söderlund, H., De Camilli, P. and Keränen, S. 1996. Yeast protein translocation complex: isolation of two genes SEB1 and SEB2 encoding proteins homologous to Sec61β-subunit. Yeast 12, 425–438.

Vanoni, M., Porro, D., Martegani, E. and Alberghina, L. 1989. Secretion of *Escheirchia coli* β-galactosidase in *Saccharomyces cerevisiae* using the signal sequence from the glucoamylase-encoding STA2 gene. Biochem. Biophys. Res. Commun. 164, 1331–1338.

Ward, M., Wilson, L. J., Kodama, K. H., Rey, M. W. and Berka, R. M. 1990. Improved production of calf chymosin in Aspergillus by expression as a glucoamylase-chymosin fusion. Bio/Technology 8, 435–440.

Zagursky, R. J., Berman, M. L., Baumeister, K. and Lomax, N. 1986. Rapid and easy sequencing of large linear double stranded DNA and supercoiled plasmid DNA. Gene Anal. Techn. 2, 89–94.

We claim:

1. A process for increasing the production of a secreted foreign or endogenous protein in a yeast cell, which process comprises:
   (a) obtaining a vector comprising an isolated DNA molecule encoding said protein;
   (b1) transforming the vector obtained into a yeast host comprising a DNA molecule encoding Seb1 protein which has an amino acid sequence depicted in SEQ ID NO:2, and overexpressing SEB1 gene, to obtain recombinant yeast host cells; or,
   (b2) transforming the vector obtained into a yeast host and retransforming this transformant with a yeast expression vector comprising a DNA molecule encoding Seb1 protein which has an amino acid sequence depicted in SEQ ID NO:2, to obtain recombinant yeast host cells overexpressing the SEB1 gene;

(c) screening for cells with enhanced production of secreted foreign or endogenous protein as compared with cells not overexpressing the SEB1 gene, and (d) cultivating said recombinant yeast host cells under conditions permitting expression of said secreted foreign or endogenous protein.

2. A process for increasing the production of a secreted foreign or endogenous protein in a yeast cell, (a) obtaining a vector comprising an isolated DNA molecule encoding said protein;

(b1) transforming the vector obtained into a yeast host overexpressing SEC61, and optionally overexpressing the SEB1 gene, to obtain recombinant yeast host cells; or, (b2) transforming the vector into a yeast host and retransforming this transformant with SEC61, and optionally with a yeast expression vector comprising a DNA molecule encoding Seb1 protein which has an amino acid sequence depicted in SEQ ID NO:2, to obtain transformed yeast host cells overexpressing SEC61; and (c) screening for cells with enhanced production of said secreted foreign or endogenous protein as compared with cells not overexpressing SEC61; and (d) cultivating said recombinant yeast host cells under conditions permitting expression of said secreted foreign or endogenous protein.

3. A process for increasing the production of an endogenous secreted protein in a yeast cell, the process comprising:

(a) transforming yeast cells producing said protein with a yeast expression vector comprising a DNA molecule encoding Seb1 protein which has an amino acid sequence depicted in SEQ ID NO:2 alone or together with SEC61;

(b) screening for transformants producing enhanced levels of said protein as compared with yeast cells not transformed, thus obtaining recombinant cells for enhanced protein production; and (c) cultivating said recombinant cells in conditions permitting expression of said protein.

4. A process for biomass production of a raw material or hydrolysis of a raw material, which process comprises:

(a) obtaining a vector comprising an isolated DNA molecule encoding an endogenous or a foreign hydrolytic enzyme;

(b1) transforming the vector obtained into a yeast host comprising a DNA molecule encoding the Seb1 protein which has an amino acid sequence depicted in SEQ ID NO:2, and overexpressing the SEB1 gene, to obtain recombinant yeast host cells; or, (b2) transforming said vector into a yeast host and retransforming this transformant with a yeast expression vector comprising a DNA molecule encoding Seb1 protein which has an amino acid sequence depicted in SEQ ID NO:2, to obtain recombinant yeast host cells overexpressing the SEB1 gene; and (c) screening for cells with enhanced production of said enzyme as compared with cells not overexpressing the SEB1 gene; and (d) cultivating said recombinant yeast host cells under conditions permitting expression of said hydrolytic enzyme wherein the raw material is produced or hydrolyzed.

5. A process for biomass production of a raw material or hydrolysis of a raw material, which process comprises:

(a) obtaining a vector comprising an isolated DNA molecule encoding an endogenous or foreign hydrolytic enzyme;

(b1) transforming the vector obtained into a yeast host overexpressing SEC61, and optionally overexpressing the SEB1 gene to obtain recombinant yeast host cells; or, (b2) transforming the vector into a yeast host and retransforming this transformant with SEC61, and optionally with a yeast expression vector comprising a DNA molecule encoding Seb1 protein which has an amino acid sequence depicted in SEQ ID NO:2, to obtain transformed yeast host cells overexpressing SEC61, and (c) screening for cells with enhanced production of said enzyme as compared with cells not overexpressing SEC61; and (d) cultivating said recombinant yeast host cells under conditions permitting expression of said hydrolytic enzyme wherein the raw material is produced and hydrolyzed.

6. Recombinant yeast cells being the cells of *Saccharomyces cerevisiae* strain VTT C-97280 having the deposit accession number DSM 11615.

* * * * *

SEQUENCE LISTING

```
<160> NUMBER OF SEQ ID NOS:  2

<210> SEQ ID NO 1
<211> LENGTH: 248
<212> TYPE: DNA
<213> ORGANISM: Saccharomyces cerevisiae
<220> FEATURE:
<221> NAME/KEY: CDS
<222> LOCATION: (1)..(246)

<400> SEQUENCE: 1 atg tca agc cca act cct cca ggt ggt caa cgt act ttg caa aag aga      48
```

-continued

```
Met Ser Ser Pro Thr Pro Pro Gly Gly Gln Arg Thr Leu Gln Lys Arg
 1               5                   10                  15 aaa cag gga agt tca caa aaa gtt gcg gca tcc gct cca aag aaa aac         96
Lys Gln Gly Ser Ser Gln Lys Val Ala Ala Ser Ala Pro Lys Lys Asn
                 20                  25                  30 acg aac agc aat aat tcg att ttg aag att tat tct gat gag gct acg         144
Thr Asn Ser Asn Asn Ser Ile Leu Lys Ile Tyr Ser Asp Glu Ala Thr
                35                   40                  45 gga cta aga gta gat ccc tta gtt gtg ttg ttt cta gcg gtc ggt ttc         192
Gly Leu Arg Val Asp Pro Leu Val Val Leu Phe Leu Ala Val Gly Phe
 50                  55                  60 atc ttt tct gtt gtt gca tta cat gtt att tct aaa gtt gcc ggt aag         240
Ile Phe Ser Val Val Ala Leu His Val Ile Ser Lys Val Ala Gly Lys
 65                  70                  75                  80 tta ttt ta                                                              248
Leu Phe
```

<210> SEQ ID NO 2
<211> LENGTH: 82
<212> TYPE: PRT
<213> ORGANISM: Saccharomyces cerevisiae

<400> SEQUENCE: 2

```
Met Ser Ser Pro Thr Pro Pro Gly Gly Gln Arg Thr Leu Gln Lys Arg
 1               5                   10                  15

Lys Gln Gly Ser Ser Gln Lys Val Ala Ala Ser Ala Pro Lys Lys Asn
                20                   25                  30

Thr Asn Ser Asn Asn Ser Ile Leu Lys Ile Tyr Ser Asp Glu Ala Thr
                35                   40                  45

Gly Leu Arg Val Asp Pro Leu Val Val Leu Phe Leu Ala Val Gly Phe
 50                  55                  60

Ile Phe Ser Val Val Ala Leu His Val Ile Ser Lys Val Ala Gly Lys
 65                  70                  75                  80

Leu Phe
```